United States Patent [19]

Waldron

[11] 4,055,185
[45] Oct. 25, 1977

[54] ROTARY DRILL FOR SURGEONS

[75] Inventor: Stephen H. Waldron, Camarillo, Calif.

[73] Assignee: American Sterilizer Company, Erie, Pa.

[21] Appl. No.: 663,070

[22] Filed: Mar. 2, 1976

[51] Int. Cl.² ............................................. A61B 17/00
[52] U.S. Cl. ..................................... 128/305.1; 32/26; 279/77; 64/4
[58] Field of Search ........................ 128/305.1, 305 R; 32/26, 28, 48, 49, 59, DIG. 1; 279/77 R, 78 R; 64/4 R, 7 R, 23 R, 26 R

[56] References Cited

U.S. PATENT DOCUMENTS

| 949,439 | 2/1910 | Rhyne | 279/77 R |
| 2,894,759 | 7/1959 | De Bruin | 279/77 R |
| 3,835,858 | 9/1974 | Hagen | 128/305 R |

Primary Examiner—Robert W. Michell
Assistant Examiner—Henry J. Recla
Attorney, Agent, or Firm—Lyon & Lyon

[57] ABSTRACT

A small housing which may be held in the hand of a surgeon has an open ended socket into which a rotary bur assembly may be inserted and latched in place. A driven gear on the rotary bur assembly meshes with a driving gear at the end of the socket. The rotary bur assembly includes a sleeve supporting the bur on axially spaced bearings, and the sleeve has an external annular shoulder. A latch moves through a side window in the housing to engage the annular shoulder to hold the gears in proper mesh, and a spring prevents accidental disengagement of the latch.

1 Claim, 9 Drawing Figures

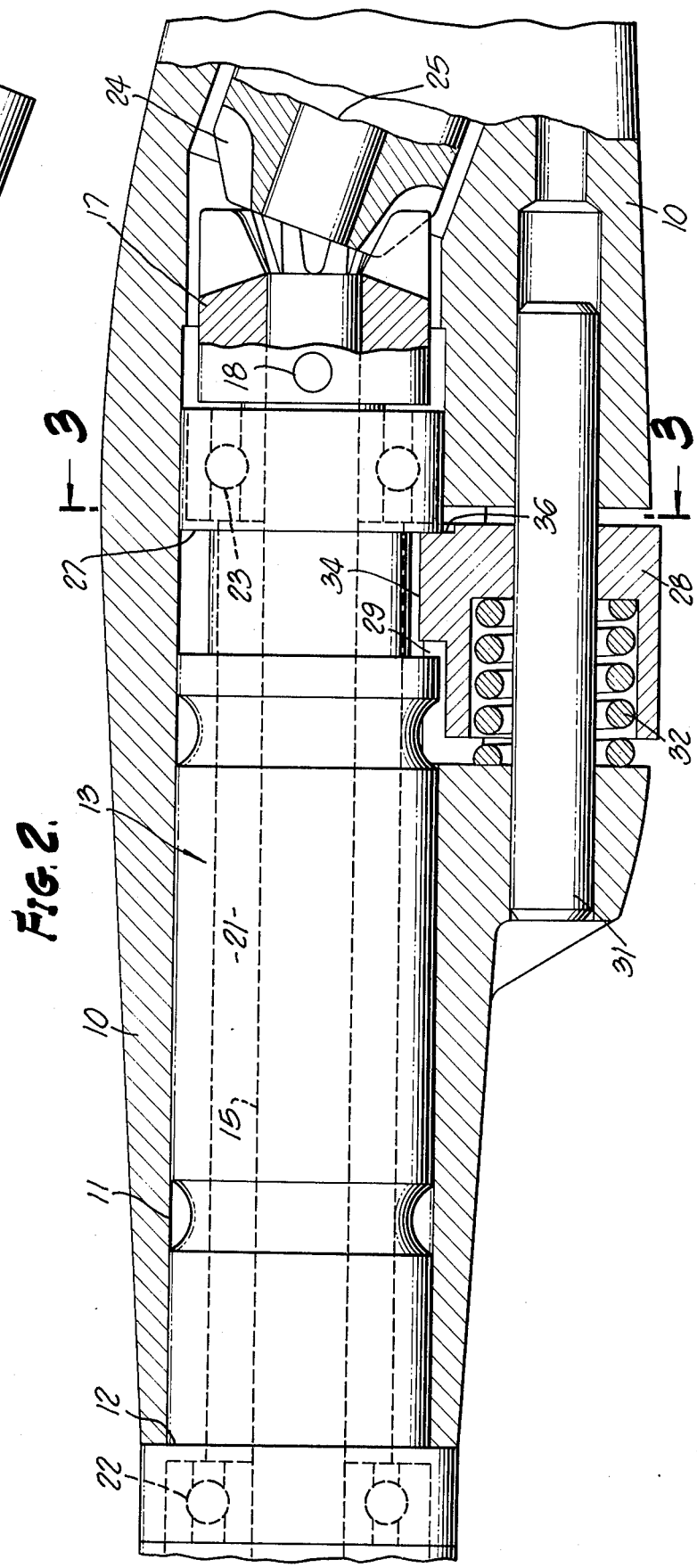

ROTARY DRILL FOR SURGEONS

This invention relates to high speed drills of the type used by surgeons for Ophthalmology and Otolaryngology. The device is designed to be used in connection with a microscope. The physical dimensions are such that there is a very narrow angle of obstructed vision.

Prior art devices of this general type have been designed to run not faster than 8000 RPM. The device of the present invention is designed to run more than twice that speed, and therefore bearings having rolling elements instead of sliding elements are required. Also, it is desired to retain the overall shape of the housing having two angularly related but integrally connected sections to conform to the shape of the surgeon's hand, and to minimize obstruction of vision. The cutting element is commonly in the form of a ball, and a typical diameter is about 1 millimeter.

It is an important object of this invention to provide a high speed drill of the type described in which the sleeve supporting the rotary bur on axially spaced antifriction bearings is positively latched in place to prevent accidental displacement but which can easily be removed and replaced with respect to the housing.

Another object is to provide a latch mechanism in which the projecting parts are very small in dimensions in order to minimize obstruction of the surgeon's vision when the device is used with a microscope.

Other and more detailed objects and advantages will appear hereinafter.

In the drawings:

FIG. 1 is a side elevation showing a preferred embodiment of this invention.

FIG. 2 is a sectional elevation partly broken away.

Figure 3:
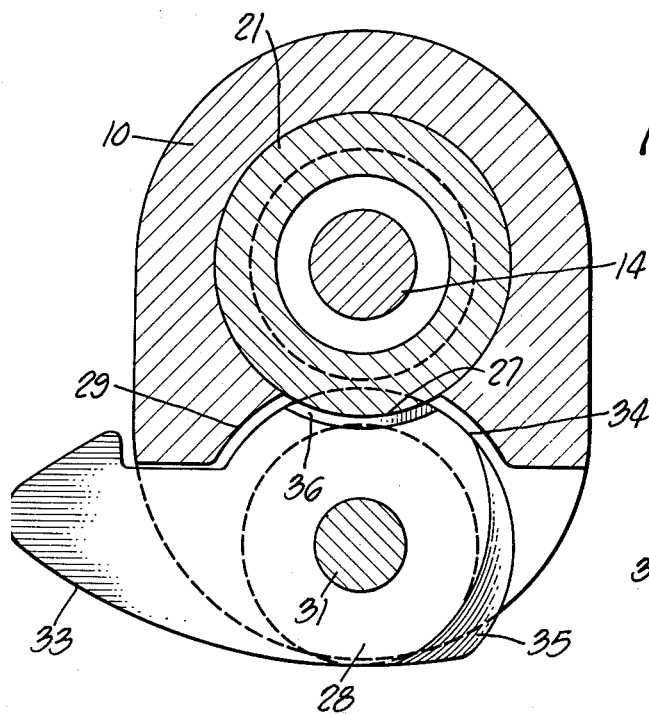
FIG. 3 is a transverse sectional view taken on the lines 3—3 as shown in FIG. 2. The latch is shown in closed position.

Referring to the drawings, the housing 10 is sized and proportioned to be grasped in one hand and is provided with an axial socket 11 open at one end 12. A rotary bur assembly generally designated 13 is received and latched in the socket 11. This rotary bur assembly includes a bur 14 having a shank 15 provided with a cutting element 16 at its projecting end. The other end of the shank 15 is fixed to a driven gear 17 by means of a transverse pin 18. The shank 15 of the bur 14 is mounted in axially spaced bearings 22 and 23 carried in the sleeve 21.

The drive gear 24 carried on a shaft 25 is driven from an air motor or other source of power connected to the housing 10 by means of the coupling 26. The drive gear 24 is mounted in a manner to minimize its axial movement. It is positioned within the housing 10 at the end of the socket 11 remote from the open end 12.

Means are provided for latching the sleeve 21 within the socket 11 of the housing 10, in a manner so that the gears 24 and 17 are in proper mesh. It will be noted that the axes of gears intersect at a small angle.

The bur 14, sleeve 21, bearings 22 and 23, and driven gear 17 are insertable as a unitary assembly into the housing socket 11 through the open end 12. This brings the driven gear 17 into mesh with the driving gear 24. Latch means are provided for securing the sleeve 21 in proper position. As shown in the drawings, this means includes an annular external shoulder 27 provided on the sleeve 21, together with a movable latch 28 which moves through a lateral window 29 in the housing 10 to engage the annular shoulder 27. The latch 28 is fixed upon a pin 31 mounted to turn in the housing 10 and extending in a direction parallel to the rotary axis of the bur 14. A coil compression spring 32 encircles the pin 31 and acts to move the latch 28 toward the right, as viewed in FIG. 2.

Figure 4:
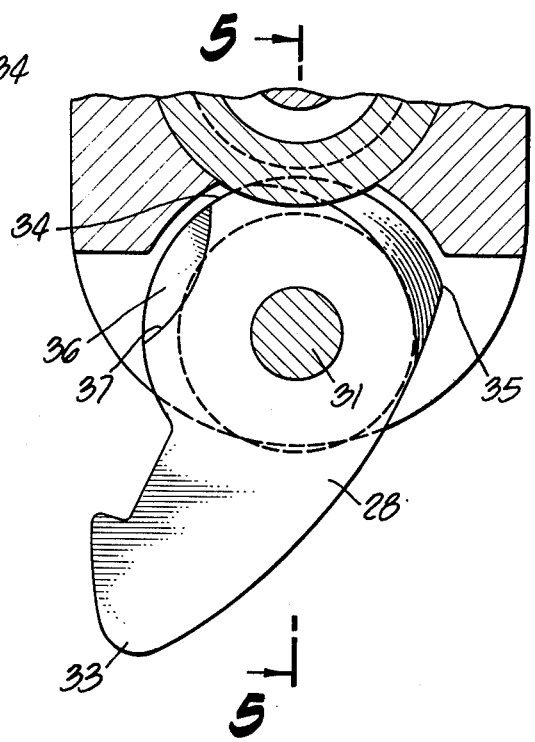
FIG. 4 is a view similar to FIG. 3, partly broken away, with the latch shown in an intermediate position.
Figure 6:
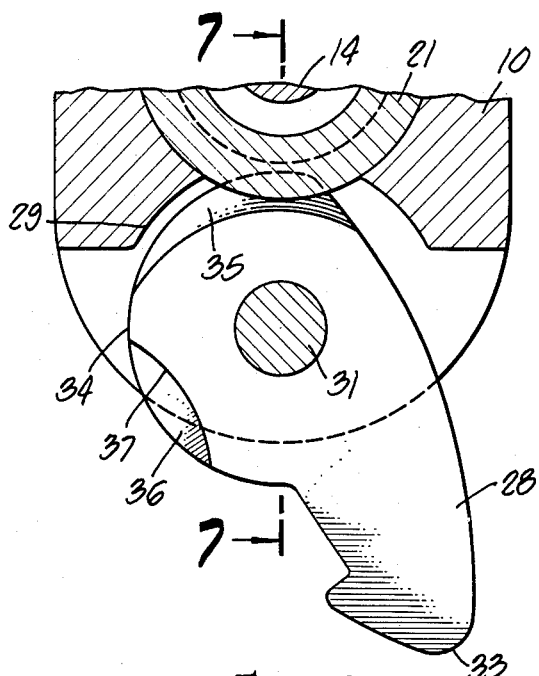
FIG. 6 is a view similar to FIG. 4, the latch being shown in another intermediate position.
Figure 7:
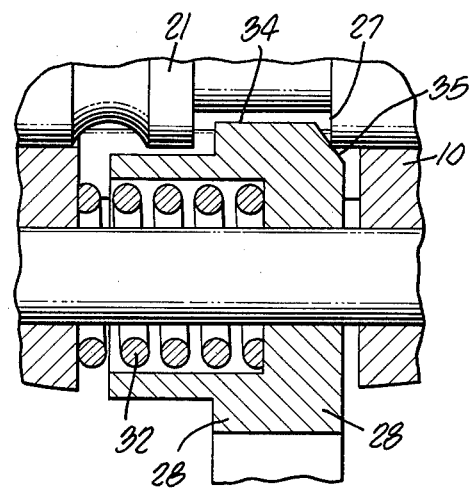
FIG. 7 is a sectional detail taken substantially on the lines 7—7 as shown in FIG. 6.
Figure 8:
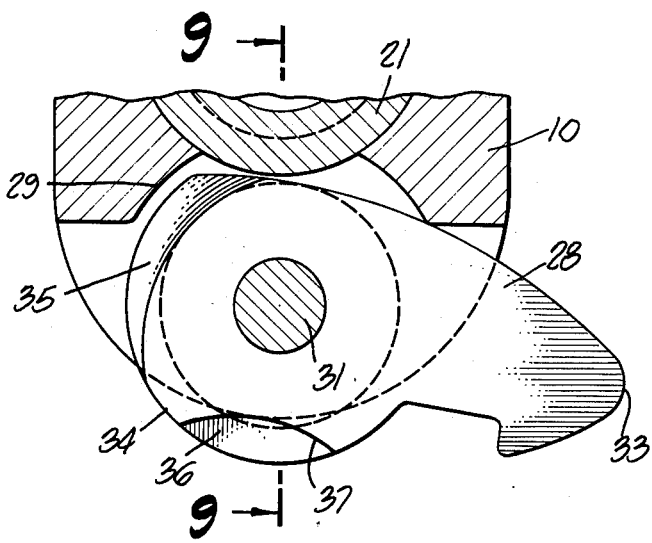
FIG. 8 is a view similar to FIG. 6, the latch being shown in fully open position.
Figure 9:
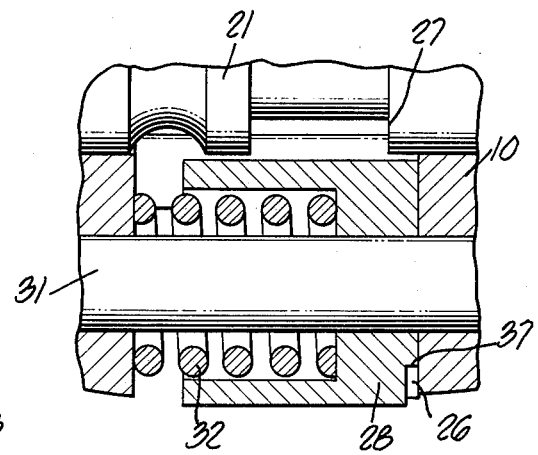
FIG. 9 is a sectional detail taken substantially on the lines 9—9 as shown in FIG. 8.

The latch 28 is provided with a projection 33 so that it may be moved manually from the fully locked position shown in FIG. 3 through the intermediate positions of FIGS. 4 and 6 to the fully open position shown in FIG. 8. The latch 28 has an arcuate surface 34 which has a tapered or beveled portion 35 and a separate detent 36 defined within the arcuate wall 37.

When the latch 28 is in the fully locked position shown in FIGS. 2 and 3, the annular shoulder 27 on the sleeve 21 projects into the shallow flat detent 36, and the arcuate wall 37 of the detent underlies a portion of the annular shoulder 27 so that the latch 28 is prevented from moving from closed position. The coil compression spring 32 holds the latch 28 against movement away from the annular shoulder 27, and hence the annular shoulder 27 remains in contact with the flat detent 36.

Figure 5:
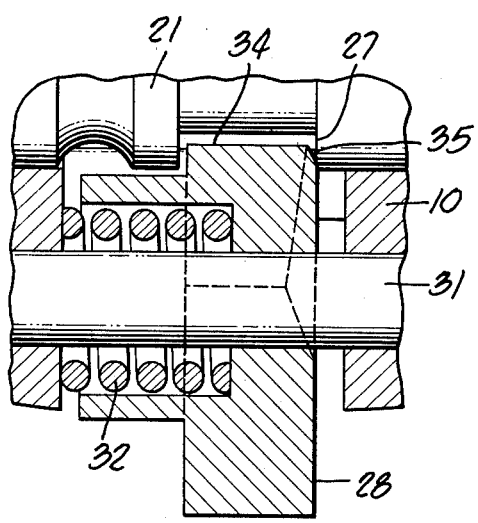
FIG. 5 is a sectional detail taken substantially on the lines 5—5 as shown in FIG. 4.

When it is desired to remove a worn bur 14 and to install a fresh one, the latch 28 is moved manually from the closed position shown in FIG. 3 to the fully open position shown in FIG. 8. In the latter position, the latch 28 is clear of all parts of the sleeve 21 so that the unitary assembly of sleeve 21, bur 14, and driven gear 17 may be withdrawn as a unitary assembly through the open end 12 of the socket 11. A similar unitary assembly with a fresh bur 14 is then inserted through the open end 12 of the socket 11 until the driven gear 17 contacts the driving gear 24. The latch 28 is then manually moved from the position shown in FIG. 8 through the intermediate position shown in FIG. 6 and FIG. 4 to the closed position shown in FIG. 3. During this swinging movement of the latch 28, the taper surface 35 engages the outer periphery of the shoulder 27 and moves the latch axially along its support pin 31 in a direction to compress the spring 32. The maximum compression of the spring occurs when the latch 28 reaches the position shown in FIG. 4. Continued clockwise movement of the latch 28 as viewed in FIG. 4 causes the detent 36 to move to the fully locked position shown in FIG. 3, at which time the latch 28 is moved toward the right as viewed in FIG. 5 for an extent equal to the depth of the detent 36. The arcuate wall 37 of the detent then cooperates with the annular shoulder 27 on the sleeve 21 to prevent accidental movement of the latch 28 away from fully locked position.

Having fully described my invention, it is to be understood that I am not to be limited to the details herein set forth but that my invention is of the full scope of the appended claims.

I claim:

1. In a rotary tool of the type described, the combination of: a manually graspable housing having an open ended socket, a rotary drive gear positioned at the end of the socket remote from the open end thereof, a rotary bur having a cutting element on one end of a shank and having a driven gear on the other end of said shank adapted to mesh with said drive gear, a sleeve encompassing said shank and having axially spaced bearings therein rotatably supporting said shank, said sleeve and bur being removably positioned as a unit in said socket in a position in which the gears are in mesh, said housing having an opening in a side thereof, said sleeve having an annular shoulder adjacent said opening, a latching device for releasably locking said sleeve against removal from said socket, said latching device including a latch mounted on the housing in said opening to turn about an axis parallel to the rotary axis of said bur, said latch being mounted for limited movement along its own axis, resilient means opposing axial movement of said latch in one direction, said latch having a taper surface engageable with said annular shoulder whereby turning of the latch about its axis serves to insure proper meshing of said gears, the latch having an arcuate detent for reception of a portion of said shoulder to hold the latch against turning movement, said resilient means acting to maintain said arcuate detent in contact with said annular shoulder.

* * * * *